(12) United States Patent
Brietzke et al.

(10) Patent No.: US 8,303,921 B2
(45) Date of Patent: *Nov. 6, 2012

(54) PROCESS FOR PRODUCING AMMONIUM SALTS

(75) Inventors: Stephan Brietzke, Altendiez (DE); Peter Groer, Rodgau (DE); Carl Christoph Mollenkopf, Frankfurt am Main (DE); Michael J. Bayer, Eschborn (DE)

(73) Assignee: Celanese International Corporation, Dallas, TX (US)

( * ) Notice: Subject to any disclaimer, the term of this patent is extended or adjusted under 35 U.S.C. 154(b) by 25 days.

This patent is subject to a terminal disclaimer.

(21) Appl. No.: 13/088,734

(22) Filed: Apr. 18, 2011

(65) Prior Publication Data

US 2011/0256045 A1 Oct. 20, 2011

Related U.S. Application Data

(60) Provisional application No. 61/428,475, filed on Dec. 30, 2010.

(30) Foreign Application Priority Data

| Apr. 19, 2010 | (EP) | .................................... 10160272 |
| Apr. 19, 2010 | (EP) | .................................... 10160275 |
| Apr. 19, 2010 | (EP) | .................................... 10160278 |

(51) Int. Cl.
*B01D 53/58* (2006.01)
*C01C 1/242* (2006.01)
(52) U.S. Cl. ........................................ 423/237; 423/549
(58) Field of Classification Search .................. 423/237, 423/549
See application file for complete search history.

(56) References Cited

U.S. PATENT DOCUMENTS

| 5,084,180 A | 1/1992 | Boateng |
| 5,808,159 A | 9/1998 | Giebeler |
| 2003/0065218 A1 | 4/2003 | Mollenkopf |
| 2009/0318685 A1 | 12/2009 | Saito |
| 2011/0256046 A1* | 10/2011 | Brietzke et al. ............... 423/237 |

FOREIGN PATENT DOCUMENTS

| CN | 1883790 A | 12/2006 |
| DE | 3522470 A1 | 1/1987 |
| DE | 3545196 A1 | 6/1987 |

(Continued)

OTHER PUBLICATIONS

English language abstract for DE 3522470 A.

(Continued)

*Primary Examiner* — Timothy Vanoy

(57) ABSTRACT

The invention relates to a process of producing an ammonium salt composition. The process comprises the step of providing a process stream comprising sulfuric acid and at least one tertiary amine. The process further comprises the step of contacting the process stream with ammonia to form a waste stream and a product stream. The waste stream comprises water, tertiary amine, and ammonia and the product stream comprises a first amount of ammonium salt. The process further comprises the step of deriving from the waste stream an off gas stream comprising a preliminary amount of ammonia. The process also comprises the step of contacting the off gas stream with an acid to form an ammonium salt stream and a purge stream. The ammonium salt stream comprises a second amount of ammonium salt and the purge stream comprises a reduced amount of ammonia, which is less than the preliminary amount.

17 Claims, 1 Drawing Sheet

FOREIGN PATENT DOCUMENTS

| | | |
|---|---|---|
| DE | 4416571 C1 | 5/1994 |
| DE | 10146689 A1 | 4/2003 |
| JP | 54032406 | 3/1979 |
| WO | 2007079944 A1 | 7/2007 |

OTHER PUBLICATIONS

English language abstract for CN 1883790 A.

English language abstract for DE 3545196 A1.

International Search Report and Written Opinion for PCT/US2011/032892 mailed Jul. 5, 2011.

Suenaga, T., "Ethylene-amine salt recovery—by converting the hydrochloride into the sulphate, and reacting with ammonia in aq. solvent to ppte. ammonium sulphate", WPI/Thompson, vol. 1979, No. 16, XP 002598345, 1979.

\* cited by examiner

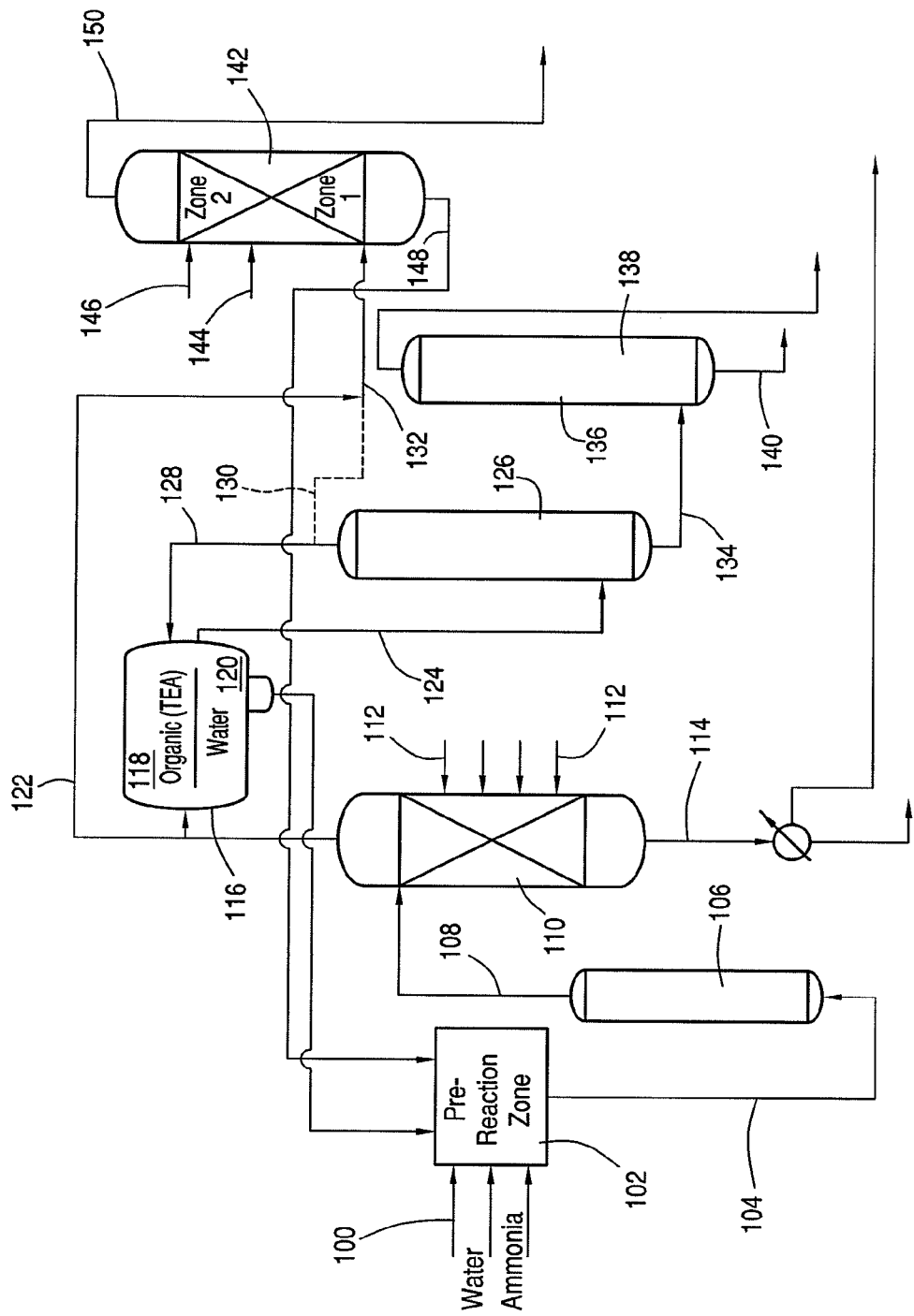

PROCESS FOR PRODUCING AMMONIUM SALTS

CROSS REFERENCE TO RELATED APPLICATIONS

This application claims priority to U.S. Provisional Application No. 61/428,475, filed on Dec. 30, 2010; European Patent Application No. 10160272.0, filed on Apr. 19, 2010; European Patent Application No. 10160275.3, filed on Apr. 19, 2010; and European Patent Application No. 10160278.7, filed on Apr. 19, 2010, the entire contents and disclosures of which are incorporated herein by reference.

FIELD OF INVENTION

The present invention relates generally to the production of ammonium salts. More specifically, the present invention relates to the production of ammonium sulfate and the recovery of tertiary organic amines from a waste stream comprising sulfuric acid.

BACKGROUND OF THE INVENTION

Many conventional chemical processes yield process waste streams comprising sulfuric acid and organic tertiary amines. The organic tertiary amines are commercially valuable and, as a consequence, it is desirable to recover the tertiary amines from the sulfuric acid. In addition, the waste sulfuric acid may be converted to ammonium sulfate, which may be used, for example, in the fertilizer industry.

DE 101 46 689 teaches one exemplary method that utilizes distillation to recover organic amines from a catalyst waste stream that contains amines. DE 35 22 470 A discloses the recovery of amine and metallic components in a polyphenylene ether synthesis waste stream via the use of a caustic soda. DE 44 16 571 discloses the recovery of amines from acidic stream by the addition of alkali bases followed by distillation until dry.

In addition, CN 1883790 describes the recovery of amines by neutralization with inorganic bases of oxide origin, e.g., NaOH, KOH, $Ca(OH)_2$, or $CaCO_3$. In this method, the sulfates that are created in side reactions must either be disposed of or processed using large amounts of energy, e.g., evaporation or drying, in order to obtain a usable product. Also, due to the molar masses of the oxide used in the reaction, the bases are often used in high amounts. In case of calcium bases, the calcium sulfate that is created precipitates during the reaction and, as such, the suspension must either be diluted or thoroughly blended, which adds to the separation cost.

Typically, when utilized as a fertilizer, an ammonium sulfate composition should comprise a low total amount of organic compounds ("TOC"). DE 35 45 196 A1 discloses the use of ammonia in a process to recover 1.) tertiary aliphatic amines, and 2.) ammonium sulfate from waste sulfuric acid. The yield of the tertiary amines recovered by this process, however, is low and, as a consequence, the TOC remaining in the ammonium sulfate is too high. Thus, this process requires further purification to reduce the TOC in the dry ammonium sulfate to an acceptable level. In addition to keeping TOC at a minimum, it is also important to keep the amount of organic tertiary amine in the ammonium sulfate composition as low as possible. The TOC may be determined according to standard method DIN EN 1484-H3.

In other conventional processes, ammonia may be utilized as the inorganic base. In these processes, however, all of the ammonia that is fed to the recovery process may not react, thus resulting in unreacted ammonia. This unreacted ammonia is problematic from efficiency and environmental perspectives.

Thus, even though conventional processes may treat the sulfuric acid-containing process streams with inorganic bases such as ammonia to recover tertiary amines and to produce ammonium sulfate, the need remains for an improved process that decreases the amount of unreacted ammonium in the final streams and increases the amount of ammonium sulfate produced.

All of the references discussed above are hereby incorporated by reference.

SUMMARY OF THE INVENTION

The present invention, in one embodiment, is to a process for producing an ammonium salt composition. The process comprises the step of providing a process stream comprising sulfuric acid and at least one tertiary amine (or a precursor thereof). The process further comprises the step of contacting the process stream with ammonia under conditions effective to form a waste stream and a product stream. The waste stream comprises water, tertiary amine, and ammonia and the product stream comprises a first amount of ammonium salt. The process further comprises the step of deriving from the waste stream an off gas stream comprising a preliminary amount of ammonia. The process further comprises the step of contacting at least a portion of the off gas stream with an acid under conditions effective to form an ammonium salt stream and a purge stream. The ammonium salt stream comprises a second amount of ammonium salt and the purge stream comprises a reduced amount of ammonia.

In another embodiment, the invention is to a process for treating an off gas stream from a potassium acesulfame production process. The process comprises the step of forming the off gas stream comprising a first amount of ammonia. The process further comprises the step of treating the off gas stream with an acid in a column to form an ammonium salt residue stream comprising an ammonium salt and a treated off gas stream comprising a reduced amount of ammonia.

BRIEF DESCRIPTION OF THE DRAWINGS

The invention is described in detail below with reference to the appended drawing.

FIG. 1 shows an ammonium sulfate production process in accordance with an embodiment of the present invention.

DETAILED DESCRIPTION OF THE INVENTION

Introduction

Conventional processes may treat waste streams that comprise sulfuric acid and organic tertiary amines with ammonia 1) to separate the organic tertiary amines and 2) to produce ammonium sulfate, which is commercially valuable in the fertilizer industry. These conventional processes, however, yield high amounts of unreacted ammonia. This unreacted ammonia typically exits the process as a vapor and is often purged and/or goes unutilized. As a result, these conventional separation processes have low overall ammonia conversions.

The present invention relates to the production of ammonium sulfate from a process stream that comprises sulfuric acid and organic tertiary amines (or precursors thereof). In the inventive process, sulfuric acid in the process stream is reacted with ammonia in a primary reaction unit to form a first amount of ammonium sulfate. Preferably, an excess of ammonia is utilized to maintain a pH value favorable for the formation of the desired products. It has now been discovered that unreacted ammonia remains from the sulfuric acid-ammonia reaction and this unreacted ammonia may be further reacted with sulfuric acid, e.g., in a secondary reaction unit, to form ammonium salt(s), e.g., additional ammonium sulfate.

As such, less ammonia is wasted and the overall conversion of the ammonia used in the acesulfame-K separation process is beneficially improved.

Generally speaking, the present invention may be utilized to recover from the sulfuric acid stream any tertiary amines. In one embodiment, the tertiary amines are those comprising up to 20 carbon atoms per nitrogen atom, e.g., up to 12 carbon atoms. Examples of the amines that can be recovered from the process sulfuric acid stream are selected from the group comprising trimethylamine, triethylamine, diethyipropylamine, tri-n-propylamine, triisopropylamine, ethyldiisopropylamine, tri-n-butylamine, triisobutylamine, tricyclohexylamine, ethyldicyclohexylamine, N,N-dimethylaniline, N,N-diethylaniline, benzyldimethylamine, pyridine, substituted pyridines such as picoline, lutidine, cholidine or methylethylpyridine, N-methylpiperidine, N-ethylpiperidine, N-methylmorpholine, N,N-dimethylpiperazine, 1,5-diazabicyclo[4.3.0]-non-5-en, 1,8-diazabicyclo-[5.4.0]-undec-7-en, 1,4-diazabicyclooctane, tetramethylhexamethylendiamine, tetramethylethylendiamine, tetramethylpropylendiamine, tetramethylbutylendiamine, 1,2-dimorpholylethan, pentamethyldiethyltriamine, pentaethyldiethylentriamine, pentamethyldipropylentriamine, tetramethyldiaminomethane, tetrapropyldiaminomethane, hexamethyltriethylentetramine, hexamethyltripropylenetetramine, diisobutylentriamine and triisopropylentriamine. Preferably, the tertiary amine comprises triethylamine.

The ammonia that can be reacted with the process stream, in some embodiments, may be used in gaseous or liquid form. In one embodiment, the partial pressure of the ammonia ranges 0.01 MPa to 30 MPa e.g., from 0.1 MPa to 10 MPa, and is limited only by the compressive strength of the equipment that is used. The ammonia may be used neat or as a mixture with other gases. The ammonia, in one embodiment, may be used as a solution in other solvents, preferably as an aqueous solution, and the aqueous solution may be obtained commercially or may be produced directly from the reaction by introducing gaseous or liquid ammonia in water. The heat of solution that is generated may either be removed or retained by transferring the heated solution to the following reaction step. To avoid the exhalation of ammonia, it is preferred to work at elevated pressure, e.g. a pressure greater than 0.1 MPa, e.g., greater than 1 MPa. In a preferred embodiment, to recover organic tertiary amines from the sulfuric acid stream, ammonia in gaseous or dissolved form may brought to the reaction with the sulfuric acid stream comprising the organic tertiary amines. Preferably, the ammonia is mixed with the sulfuric acid in an amount sufficient to obtain a pH greater than 9.5, e.g., greater than 10 or greater than 10.5. According to a preferred embodiment, the pH in the sulfuric acid-ammonia reaction ranges 9.8 to 12, e.g., from 10 to 11.5. In one embodiment, the ammonia is added to the sulfuric acid in an amount sufficient to obtain these ranges.

Suitable process streams that may be utilized in the inventive process preferably contain from 0.1 wt % to 100 wt % of tertiary amines (optionally in the precursor form of the respective organyl ammonium hydrogen sulfate), e.g., from 1 wt % to 75 wt % or from 10 wt % to 50 wt %. Solutions may also contain free sulfuric acid and water. In one embodiment the process stream for example, comprises 35 wt % triethylammonium hydrogen sulfate, 45 wt % sulfuric acid, 16 wt % water, and minor amounts of organic components.

Without being bound by theory, it is believed that during the reaction of sulfuric acid with ammonia, the free sulfuric acid is neutralized. This neutralization may be followed by conversion of organyl ammonium hydrogen sulfate to the corresponding amines. The reaction may be conducted batchwise, e.g. in an agitating machine, or continuously, e.g., in a pump reactor with or without agitation means. In the latter case, a static mixer is also a suitable reactor. In this case, the static mixer may be equipped with a temperature equalizer. Preferably, the reaction is conducted in a plug flow reactor. The plug flow reactor is preferred because it allows the reaction to be conducted at elevated pressure and elevated temperature.

The reaction preferably is conducted at an elevated pressure, e.g., from 0.2 MPa to 1.2 MPa or from 0.7 MPa to 1.0 MPa. The reaction preferably is conducted at temperatures ranging from 95° C. to 150° C., e.g., from 100° C. to 140° C. or from 110° C. to 130° C.

In one embodiment, in order to avoid precipitation of the ammonium sulfate by exceeding the solubility limit during or after the reaction, water is added to the reaction mixture. This addition may be performed by diluting the employed sulfuric acid with water before the reaction, by adding water during the reaction, or by diluting the obtained ammonium sulfate solution after completion of the reaction.

The reaction heat that is produced may be removed using typical cooling devices known in the art. According to a preferred embodiment, however, the released reaction heat is used in a subsequent separation step, e.g., in a distillation of the organic tertiary amines. In case the reaction has been conducted under pressure and elevated temperature, the expanded reaction mixture may be directly conveyed to a distillation column. Preferably, the inventive process is performed at temperatures at or above the boiling point of the free amine, or at or above the boiling point of the amine/water azeotrope, if this azeotrope is present. For example, in the case of triethylamine, the preferred temperature ranges from 75° C. to 105° C. at 1 bar. In case the reaction heat is not sufficient for distillation, additional heating may be utilized.

In another embodiment, the energy from the reaction is at least partially used to evaporate the water in the ammonium sulfate to yield solid ammonium sulfate, e.g., the reaction heat may be used to evaporate water from the aqueous ammonium sulfate solution that is produced.

In one embodiment, the organic tertiary amines formed in the sulfuric acid-ammonia reaction are separated from the reaction mixture. In preferred embodiments, during the separation, the pH of the reaction mixture is adjusted at a pH greater than 9.5, e.g., greater than 10 or greater than 10.5. Preferably the pH is adjusted such that the pH ranges from 9.8 to 12, e.g., from 10 to 11.5.

The separation of the released amines from the reaction mixture, in one embodiment, may be performed by distillation, extraction, and/or phase separation. Distillation is preferred for amines having a low boiling point and/or amines having good water solubility. Distillation also is preferred where the amines form an azeotrope with water. Distillation may be performed directly from the reaction vessel or in a two stage apparatus.

According to a preferred embodiment, the thermal energy of the products obtained at the head of the distillation column may be used to heat the feed flow, e.g. the ammonia feed or the feed comprising the reaction mixture.

In one embodiment, low solubility amines that are in the ammonium sulfate solution may be separated through phase separation. In another embodiment, the ammonium sulfate solution is extracted with a suitable solvent. Preferably, the organic tertiary amine is separated from the reaction mixture by extraction with an organic liquid, preferably a liquid hydrocarbon. In one preferred embodiment, the organic liquid comprises an aliphatic liquid hydrocarbon comprising at least 8 carbon atoms, e.g., at least eight carbon atoms, most preferably being octane. The methods for the separation of the organic amines may be applied individually or in combination.

In one embodiment, the organic tertiary amine, e.g., triethylamine, is separated from the sulfuric acid-ammonia reaction mixture in a distillation column and, in order to maintain a pH of 9.5 or higher during the separation in the distillation column, ammonia is added thereto. Preferably, the ammonia is added to the distillation column counter to the flow the reaction mixture. In one embodiment, during the distillation, the sulfuric acid-ammonia reaction mixture is continuously fed to the upper part of a distillation column and the ammonia is continuously fed at the lower part or the middle part of the distillation column. The position of the ammonia feed may be used to control the pH of the reaction mixture being separated. The amount of ammonia and, consequently, the adjusted pH value, influence the capacity of the column with respect to separation of the tertiary amines from the aqueous ammonium sulfate solution. The closer the ammonia feed is to the bottom of the distillation column, the higher the pH of the reaction mixture in the bottom of the column.

Also, the position of the ammonia feed to the distillation column also may influence the pH of the aqueous solution comprising ammonium sulfate, which exits the bottom of the separation unit, e.g., distillation column. In a preferred embodiment, the ammonia feed is positioned on the distillation column such that the aqueous ammonium sulfate solution, which is essentially free of the organic tertiary amine, in the lower part of the column has a pH ranging from 5 to 7, e.g., from 5.5 to 6.5.

In one embodiment, the inventive process further comprises the step of dewatering the recovered tertiary amine, which can optionally be followed by further distillation of the dewatered amine. Preferably, the organic tertiary amine, e.g., triethylamine, is recovered in a yield of at least 99.0%, e.g., at least 99.5% or at least 99.9%.

In another embodiment, the inventive process forms ammonium sulfate as product. The ammonium sulfate solution, thus formed, provides a quickly recoverable, easily dosable, valuable nitrogen fertilizer. In one embodiment, no additional processing of the ammonium sulfate is required prior to use. The ammonium sulfate content of the solution may be controlled by adjusting 1) the water content of the reactant sulfuric acid, 2) the addition of water before, during or after the reaction and/or 3) distillation of water taking into account the solubility limit of ammonium sulfate in water. In one embodiment, the ammonium sulfate solution is purified, e.g., distilled or spray dried, to remove substantially all of the water therefrom. The solid ammonium sulfate, thus produced, may be used as a fertilizer.

The reaction of the ammonia and the sulfuric acid, as discussed above, yields a product mixture comprising water, the tertiary amine, ammonia, e.g., unreacted ammonia, and ammonium salt, e.g., ammonium sulfate. Preferably, the subsequent separation step yields a waste stream comprising water, the tertiary amine, and ammonia, and a product stream comprising ammonium salt, e.g., a first amount of ammonium salt.

The inventive process, in some embodiments, further comprises the step of deriving from the waste stream an off gas stream comprising ammonia, e.g., a preliminary amount of ammonia, and optionally a first amount of methylene dichloride. Thus, the waste stream may be processed to separate, among others, the unreacted ammonia, the methylene dichloride, and/or the tertiary amine(s) therefrom. The preliminary amount of ammonia in the off gas preferably comprises at least a portion of the unreacted ammonia that remains from the ammonia utilized to contact the process stream. In some embodiments, the off gas is derived directly from the reaction vessel. Preferably, the reaction mixture is condensed to yield a liquid stream and a vapor stream. The liquid stream may be directed to a decanter and the vapor stream, which comprises unreacted ammonia and methylene dichloride, may be directed to further processing. In preferred embodiments, the off gas comprises at least a portion of the vapor stream.

In some embodiments, the process further comprises the step of contacting the off gas stream with an acid, e.g., sulfuric acid, under conditions effective to form an ammonium salt stream and a purge stream. Preferably, in doing so, at least 75 mol % of the ammonia in the off gas is converted, e.g., at least 95 mol % or at least 98 mol %. In a preferred embodiment, the off gas is contacted in at least one secondary reaction unit, e.g., a reactive distillation column or a washing column. In one embodiment, the secondary reaction unit comprises a washing column, which employs a sulfuric acid washing agent. The secondary reaction may also comprise multiple reactions units, e.g., multiple reactors and/or multiple columns. In one embodiment, the off gas is contacted in a reactive distillation column and any remaining unreacted ammonia is further reacted with sulfuric acid in a washing vessel. The ammonium salt stream comprises a second amount of ammonium salt, which is in addition to the ammonium salt produced in the primary reactor(s).

Thus, by contacting the unreacted ammonia in the off gas with acid, the overall ammonia conversion of the process is improved as compared to conventional processes, which waste the unreacted ammonia and fail to convert unreacted ammonia, e.g., to ammonium salt. As a result of the improved conversion of ammonia, overall production of ammonium salt, e.g., ammonium sulfate, for the process as a whole is improved.

In addition, in some embodiments, the off gas stream feeding the unit in which the secondary reaction occurs, e.g., the washing column, comprises lower amounts of ammonia. Typical contacting units may not be configured as is the contacting unit of the present invention. As such, the conventional contacting units use feed streams comprising significantly higher amounts of ammonia.

Exemplary Ammonium Salt Production Process

FIG. 1 shows an exemplary ammonium salt production process in accordance with embodiments of the present invention. Process stream 100 comprises sulfuric acid and at least one tertiary amine (optionally in the form of the respective organyl ammonium hydrogen sulfate) and water. In a preferred embodiment, process stream 100 is a waste stream from an acesulfame-K production process, e.g., at least a portion of an aqueous sulfuric acid phase from an acesulfame-K production process, as discussed below. Exemplary ranges for some of the components of the process stream are shown in Table 1.

TABLE 1

| PROCESS STREAM COMPOSITION | | | |
|---|---|---|---|
| | Conc. (mol %) | Conc. (mol %) | Conc. (mol %) |
| Sulfuric Acid | 1 to 99 | 30 to 65 | 35 to 55 |
| Trialkylammonium Ammonium Hydrogen Sulfate | 1 to 75 | 25 to 45 | 30 to 40 |
| Water | 1 to 99 | 5 to 50 | 10 to 25 |
| Organics | Less than 1 | Less than 0.5 | Less than 0.1 |

As shown in FIG. 1, pre-reaction zone 102 receives process stream 100. Pre-reaction zone 102 prepares the reactants, e.g., sulfuric acid, water, and ammonia, for separation of the tertiary amines and/or conversion of sulfuric acid to ammonium sulfate. In one embodiment, in pre-reaction zone 102, ammonia, e.g., gaseous ammonia, is fed to a first plug flow reactor, where the ammonia is diluted with water. The water may be provided to the first plug flow reactor from a water reservoir. The aqueous ammonia solution, thus formed, exits the first plug flow reactor is conveyed to a second plug flow reactor, where the ammonia solution contacts the acesulfame-K waste stream. The waste stream fed to the second plug flow reactor may be fed from a waste stream reservoir. The acesulfame-K waste stream/ammonia product stream exits the second plug flow reactor, thus exiting pre-reaction zone 102, and is directed via line 104 to reactor 106.

In reactor 106 sulfuric acid from the process stream contacts, e.g., reacts with, ammonia to form ammonium sulfate. In some embodiments, at least 50% of the sulfuric acid in process stream 100 is converted to ammonium sulfate in reactor 106, e.g., at least 90% or at least 95%. Reactor 106 preferably yields a crude product comprising ammonium sulfate, triethylammonium sulfate, triethylamine, water, and unreacted ammonia. Reactor 106 is preferably a plug flow reactor, but other suitable reactor types, such as a stirred tank reactor or other tube-style reactors, may be employed as well. The reaction in reactor 106 is, in one embodiment, conducted under an elevated pressure, for example at a pressure ranging from 2 to 12 bar, e.g., from 7 to 10 bar, and at temperatures ranging from 95° C. to 140° C., e.g., from 100° C. to 126° C. or from 110° C. to 130° C.

In preferred embodiments, this reaction is carried out under basic conditions, e.g., the reaction is maintained at a high pH. In one embodiment, the pH of the reaction mixture is maintained at a level at least 8, at least 9, at least 9.5 or at least 10. In terms of ranges, the pH of the reaction mixture may be maintained at a level ranging from 8 to 12, e.g., from 9 to 12, or from 10 to 11.5. In one embodiment, the high pH level is maintained by mixing ammonia with the waste sulfuric acid. Maintaining the pH at these levels provides for 1) efficient tertiary amine separation, 2) efficient sulfuric acid conversion, and 3) a product ammonium sulfate having a low TOC, e.g., less that 1 wt % organic content or less than 0.5 wt % organic carbon content, based on the total amount of dried ammonium sulfate obtained.

In a preferred embodiment, water is added to the reaction mixture to avoid precipitation of ammonium sulfate, which occurs as the solubility limit is exceeded during or after the reaction. This precipitation may be avoided, for example, by diluting process stream 100 with water prior to reactor 106, or by adding water to reactor 106, or by diluting the reaction solution.

Although FIG. 1 shows one reactor, there may be multiple reactors for reacting the process stream and aqueous ammonia stream.

In a preferred embodiment, the sulfuric acid and the ammonia are reacted in reactor 106 and are further reacted and/or separated in separation unit, e.g., reactive distillation column, 110. In this case, the reaction mixture exits reactor 106 and is directed via line 108 to separation unit 110. Separation unit 100 is preferably a distillation column, e.g., a reactive distillation column, however, other suitable separation units, such as extractors and phase separators may be employed. Distillation is especially advantageous in cases where the amines in the product stream have a low boiling point, are highly soluble in water, and/or form an azeotrope with water. Although FIG. 1 shows a single separation unit, multiple separation units may also be employed.

In one embodiment, separation unit 110 is operated under basic conditions. Preferably, these basic conditions are achieved by adding ammonia, e.g., via ammonia feeds 112. In one embodiment, the pH of the distillation fluid in separation unit 110 is maintained at a level at least 8, at least 9, at least 9.5 or at least 10. In terms of ranges, the pH of the distillation fluid may be maintained at a level ranging from 8 to 12, e.g., from 9 to 12, or from 10 to 11.5. Also, ammonia may be added to react with sulfuric acid present in separation unit 110 to form ammonium sulfate. Ammonia is added in a molar excess in separation unit, such that the molar ratio of ammonia to sulfuric acid is greater than 1.2:1, e.g., greater than 1.5:1. The excess molar ratio is needed to ensure complete reaction of the sulfuric acid.

Separation unit 110 yields a residue comprising an ammonium salt, e.g., ammonium sulfate, which exits separation unit 110 via line 114, and a distillate comprising triethylamine, water, unreacted ammonia, methylene dichloride, and acetone. In one embodiment, the distillate comprises a triethylamine-water azeotrope.

The distillate from separation unit 110, in one embodiment, is condensed to yield a liquid stream and a vapor stream. The liquid stream is conveyed to phase separation unit 116, which is preferably a decanter. Phase separation unit 116 separates the liquid phase of the distillate into upper liquid organic phase 118, which comprises triethylamine, and lower liquid aqueous phase 120, which comprises water. The vapor stream, e.g., at least a portion of the off gas, comprising methylene dichloride and ammonia, e.g., a preliminary amount of ammonia, exits separation unit 110 and, once separated from the liquid phase, is directed to further processing. In one embodiment, the off gas further comprises acetone. In one embodiment, the off gas comprises from 25 mol % to 99.9 mol % ammonia, based on the total weight of the off gas, e.g., from 50 mol % to 99 mol % or from 75 mol % to 98 mol %. In terms of upper limits, the off gas may comprise less than 99.9 mol % ammonia, e.g., less than 99 mol % or less than 98 mol %. It is appreciated that the off gas may contain a significant amount of ammonia. In terms of lower limits, the off gas may comprise at least 50 mol % ammonia, e.g., at least 75 mol % or at least 90 mol %.

Upper liquid organic phase 118 is directed via line 124 to column 126, which preferably is a dewatering column. Column 126 separates upper liquid organic phase 118 into a distillate comprising a water/triethylamine azeotrope and optionally ammonia and a residue comprising triethylamine. At least a portion of the water/triethylamine azeotrope is recycled to phase separation unit 116 via line 128. In one embodiment, at least a portion of the ammonia in the distillate of column 126 is combined with line 122 via optional line 130 to form combined ammonia feed line 132. The triethylamine-containing residue is directed via line 134 to column 136, which is preferably a distillation column. Column 136 separates the contents of line 134 into a triethylamine distillate and a residue comprising high boiling point organic compounds. The distillate from column 136 comprises purified triethylamine is withdrawn via line 138 and is optionally recycled to an acesulfame-K production process (not shown). The residue exits column 136 via line 140 and is disposed accordingly.

The off gas in line 122 exiting phase separation unit 116 is optionally combined with ammonia in line 130 and directed to column 142 via line 132. Column 142 is, for example, a washing column or a reactive distillation column. In column 142, the ammonia-containing off gas is contacted with sulfuric acid from sulfuric acid feed 144 to form ammonia salts, e.g., ammonium sulfate. The ammonium sulfate exits column 142 as a residue via line 148. Preferably, the ammonium sulfate-containing residue from column 142 is recycled to separation unit 110 (via pre-reaction zone 102), where the additional ammonium sulfate may be recovered in the residue of separation unit 110. Water may also be provided to column 142 via water feed 146. Unreacted ammonia, if any, exits column 142 as an exhaust distillate, e.g., a purge stream, via line 150. Preferably, 1) the acid is provided to column 142 in a first zone, wherein acid reacts with the ammonia to form the ammonium salts; and 2) water is added in a second zone to dissolve any remaining ammonia.

Preferably, the reaction in the secondary reactor is conducted in a neutral or acidic environment so as to better neutralize the ammonia being fed thereto. In one embodiment, the pH in the secondary reactor is less than 8, e.g., less than 7, or less than 6. In terms of ranges, the pH in the secondary reactor may be maintained at a level ranging from 0.1 to 8, e.g., from 1 to 6.

In a preferred embodiment, multiple units are utilized to react the ammonia in the off gas with ammonia to form ammonium sulfate. As one example (not shown), an additional washing unit may be employed to react unreacted ammonia that remains in the exhaust distillate. The additional washing unit may be any suitable unit, preferably being a washing vessel having an acid feed.

In other embodiments, the off gas is contacted in a suitable reaction unit other than a column, e.g., a reactor, a scrubber, a spray tower, or a tube-style reactor. Methods of contacting the reactants are well known in the art and it is well within the skill of the art to utilize an appropriate unit to perform the contacting step.

As a result of the secondary reaction of acid with the unreacted ammonia in line 132, additional ammonium sulfate is advantageously formed. Conventionally, the unreacted ammonia in line 132 would be purged or otherwise disposed. As such, column 142 provides an exhaust distillate that exits via line 150 and comprises little, if any ammonia, e.g., less than 10 mol % ammonia, less than 5 mol % ammonia, or less than 3 mol % ammonia. The distillate in line 150 may, also comprise a significant portion of any solvents that may be used throughout the inventive process or that may be present in the initial process stream, e.g., methylene dichloride. In one embodiment, exhaust distillate 150 comprises a reduced amount of ammonia (as compared to the preliminary amount of ammonia). In one embodiment, the reduced amount of ammonia is at least 90% less than the preliminary amount of ammonia, e.g., at least 95% or at least 98%. In another embodiment, the exhaust distillate stream comprises no ammonia, e.g., the preliminary amount of ammonia is reduced to nothing. As a result of the ammonium sulfate formation from the unreacted ammonia, a low ammonia content exhaust distillate exits column 142 and may be released safely.

As a result of the secondary reaction step, a high percentage of the total amount of ammonia fed to the process is converted, preferably, at least 90 mol % of a total amount of ammonia fed to the process, e.g., at least 95 mol % or at least 98 mol %. In these embodiments, the total amount of ammonia comprises all of ammonia streams fed to the process including ammonia in the process stream, ammonia fed to pre-reaction zone 102, and the ammonia fed via ammonia feed line(s) 112. In one embodiment, because the unreacted ammonia is converted rather than being wasted, the reduced amount of ammonia in the line 150 is less than 10% of a total amount of ammonia fed to the process, e.g., less than 5% or less than 3%. In some embodiments, the expected overall ammonium salt production is based on the conversion of sulfuric acid in the waste stream and the ammonium salt selectivity. Thus, the expected production of ammonium sulfate (in moles) in these instances, would be the moles of sulfuric acid converted multiplied by the ammonium salt selectivity. Preferably, the overall ammonium salt production is greater than the expected production of ammonium salt, e.g., at least 10% greater, at least 15% greater, or at least 25% greater.

In preferred embodiments, the acid used to contact the off gas is sulfuric acid, and the resultant ammonium salt comprises ammonium sulfate. However, in other embodiments, acids other than sulfuric acid may be employed. In such cases, the resultant ammonium salt will correspond to the acid that is employed. For example, if phosphoric acid were utilized, the resultant ammonium salt would comprise ammonium phosphate.

The contents of line 150 then may be further processed to recover the components thereof. As one example, the overhead stream in line 150 may be contacted with an adsorbent composition, e.g., polyethylene glycol ether, to form a purified methylene dichloride stream comprising methylene dichloride and a small amount of impurities, e.g., ammonia.

The ammonium sulfate production process of the present invention may be used with any suitable process stream comprising a suitable acid. In a preferred embodiment, the process stream comprises an acesulfame-K waste stream that results from an acesulfame-K production process. One exemplary process reacts sulfamic acid and/or a salt thereof and diketene may be reacted to form an acetoamide salt, e.g., acetoacetamide-N-sulfonate triethylammonium salt. In preferred embodiments, the acetoamide salt serves as an intermediate in the formation of the cyclized acesulfame-H. The reaction product containing the acetoacetamide salt is then cyclized, preferably utilizing sulfur trioxide. The cyclized product is then hydrolized to form acesulfame-H, the acid form of acesulfame-K. The hydrolysis reaction is preferably carried out via addition of water (or ice) and optionally aqueous sulfuric acid.

The hydrolysis reaction yields a multiple phase mixture, which is directed to a phase separation unit, e.g., decanter. The decanter separates the multiple phase mixture into an organic phase, an aqueous phase (sulfuric acid phase), and optionally a solid precipitate phase. The aqueous phase comprises sulfuric acid and at least one tertiary amine. As such, this aqueous phase may serve as a process stream for use in embodiments of the present invention.

While the invention has been described in detail, modifications within the spirit and scope of the invention will be readily apparent to those of skill in the art. In view of the foregoing discussion, relevant knowledge in the art and references discussed above in connection with the Background and Detailed Description, the disclosures of which are all incorporated herein by reference. In addition, it should be understood that aspects of the invention and portions of various embodiments and various features recited below and/or in the appended claims may be combined or interchanged either in whole or in part. In the foregoing descriptions of the various embodiments, those embodiments which refer to another embodiment may be appropriately combined with other embodiments as will be appreciated by one of skill in the art. Furthermore, those of ordinary skill in the art will appreciate that the foregoing description is by way of example only, and is not intended to limit the invention.

We claim:

1. A process of producing an ammonium salt composition, comprising the steps of:
   (a) providing a process stream comprising sulfuric acid and at least one tertiary amine or a precursor thereof;
   (b) contacting the process stream with ammonia under conditions effective to form a waste stream comprising water, the tertiary amine, and ammonia and a product stream comprising a first amount of ammonium salt;
   (c) deriving from the waste stream an off gas stream comprising a preliminary amount of ammonia; and
   (d) contacting at least a portion of the off gas stream with an acid under conditions effective to form an ammonium salt stream comprising a second amount of ammonium salt and a purge stream comprising a reduced amount of ammonia.

2. The process of claim 1, wherein the acid in step (d) is sulfuric acid and the ammonium salt is ammonium sulfate.

3. The process of claim 1, wherein the purge stream further comprises nitrogen, acetone, dichloromethane, organics, and water.

4. The process of claim 1, wherein the deriving comprises separating the waste stream into a vapor stream, a liquid organic phase comprising the at least one tertiary amine, and an aqueous phase, and wherein the vapor stream comprises the off gas stream.

5. The process of claim 1, wherein step (b) is performed in a first reactor and wherein the process further comprises recycling the ammonium salt residue stream to the first reactor.

6. The process of claim 1, wherein at least 90 mol % of a total amount of ammonia fed to the process is converted.

7. The process of claim 6, wherein the total amount of ammonia fed to the process comprises the ammonia used in step (b).

8. The process of claim 1, wherein the reduced amount of ammonia in the purge stream is less than 10% of a total amount of ammonia fed to the process.

9. The process of claim 1, wherein the reduced amount is at least 90% less than the preliminary amount.

10. The process of claim 1, wherein an overall production of ammonium salt is greater than an expected production of ammonium salt wherein the expected production of ammonium salt is based on the conversion of sulfuric acid in the waste stream and the ammonium salt selectivity.

11. The process of claim 1, wherein the purge stream further comprises a first amount of methylene dichloride, and wherein the process further comprises contacting the purge stream with an adsorbent composition to form a purified stream comprising a reduced amount of methylene dichloride.

12. The process of claim 1, wherein the adsorbent comprises polyethylene glycol ether.

13. A process for treating an off gas stream from a potassium acesulfame production process, comprising the steps of
   (a) forming the off gas stream comprising a first amount of ammonia;
   (b) treating the off gas stream with an acid in a column to form an ammonium salt residue stream comprising an ammonium salt and a treated off gas stream comprising a reduced amount of ammonia.

14. The process of claim 13, wherein the forming comprises the steps of:
   providing a potassium acesulfame process stream comprising sulfuric acid and tertiary amines;
   contacting the process stream with ammonia under conditions effective to form a waste stream comprising water, the tertiary amine, and ammonia and a product stream comprising ammonium sulfate; and
   deriving from the distillate the off gas stream.

15. The process of claim 14, wherein the deriving comprises the step of:
   separating the waste stream into a vapor stream, a liquid organic phase comprising the tertiary amines, and an aqueous phase, and wherein the vapor stream comprises the off gas stream.

16. The process of claim 13, wherein in the treated off gas comprises less than 10 mol % ammonia.

17. A method of producing an ammonium salt composition, comprising the steps of:
   (a) providing a process stream comprising sulfuric acid, methylene dichloride, water, and a tertiary amine;
   (b) contacting the process stream with ammonia under conditions effective to form a waste stream comprising ammonia, water, the tertiary amine, and the methylene dichloride, and a product stream comprising a first amount of ammonium salt;
   (c) deriving from the waste stream an off gas stream comprising a preliminary amount of ammonia and methylene dichloride;
   (d) contacting the off gas stream with an acid under conditions effective to form an ammonium salt stream comprising a second amount of ammonium salt and an overhead stream comprising methylene dichloride and a reduced amount of ammonia based on the preliminary amount of ammonia; and
   (e) contacting the overhead stream with an adsorbent under conditions effective to reduce the amount of methylene dichloride contained therein.

* * * * *